US00PP31436P2

(12) United States Plant Patent
Sheehan

(10) Patent No.: US PP31,436 P2
(45) Date of Patent: Feb. 11, 2020

(54) GRAPEVINE PLANT NAMED 'SHEEGENE 102'

(50) Latin Name: *Vitis vinifera*
Varietal Denomination: Sheegene 102

(71) Applicant: Sheehan Genetics Austrailia PTY, Ltd., Mildura (AU)

(72) Inventor: Timothy P. Sheehan, Vancouver, WA (US)

(73) Assignee: Sheehan Genetics Austrailia PTY, Ltd., Mildura (AU)

( * ) Notice: Subject to any disclaimer, the term of this patent is extended or adjusted under 35 U.S.C. 154(b) by 0 days.

(21) Appl. No.: 16/350,751

(22) Filed: Jan. 2, 2019

(51) Int. Cl.
*A01H 5/08* (2018.01)
*A01H 6/88* (2018.01)

(52) U.S. Cl.
USPC ..... Plt./205

(58) Field of Classification Search
USPC ..... Plt./205
CPC ..... A01H 5/08; A01H 6/88
See application file for complete search history.

(56) References Cited

U.S. PATENT DOCUMENTS

| | | | |
|---|---|---|---|
| PP4,787 | P | 11/1981 | Olmo |
| PP17,211 | P2 | 11/2006 | Gargiulo |
| PP17,504 | P3 | 3/2007 | Maranto |
| PP17,875 | P3 | 7/2007 | Gargiulo |
| PP18,226 | P3 | 11/2007 | Gargiulo |
| PP18,959 | P2 | 6/2008 | Sheehan |
| PP18,960 | P2 | 6/2008 | Sheehan |
| PP18,987 | P2 | 6/2008 | Sheehan |
| PP19,041 | P2 | 7/2008 | Sheehan |
| PP19,599 | P2 | 12/2008 | Maranto |
| PP19,911 | P2 | 4/2009 | Sheehan |
| PP19,912 | P2 | 4/2009 | Sheehan |
| PP20,110 | P3 | 6/2009 | Sheehan |
| PP20,236 | P3 | 8/2009 | Sheehan |
| PP20,252 | P3 | 9/2009 | Sheehan |
| PP20,281 | P3 | 9/2009 | Sheehan |
| PP20,317 | P3 | 9/2009 | Sheehan |
| PP20,753 | P3 | 2/2010 | Sheehan |
| PP21,075 | P2 | 6/2010 | Maranto |
| PP21,316 | P3 | 9/2010 | Sheehan |
| PP23,125 | P2 | 10/2012 | Sheehan |
| PP23,478 | P3 | 3/2013 | Chimenti |
| PP23,837 | P3 | 8/2013 | Sheehan |
| PP25,095 | P3 | 11/2014 | Sheehan |
| PP25,131 | P3 | 12/2014 | Sheehan |
| PP26,179 | P3 | 12/2015 | Sheehan |
| PP26,300 | P3 | 1/2016 | Lombard |
| PP28,269 | P3 | 8/2017 | Sheehan |
| PP29,129 | P2 | 3/2018 | Sheehan |
| 2008/0201809 | P1 | 8/2008 | Sheehan |
| 2013/0276181 | P1 | 10/2013 | Sheehan |
| 2016/0044845 | P1 | 2/2016 | Sheehan |

OTHER PUBLICATIONS

U.S. Appl. No. 16/350,750, filed Jan. 2, 2019, Sheehan.
U.S. Appl. No. 16/350,752, filed Jan. 2, 2019, Sheehan.
Application for Plant Breeder's Rights for Grapevine ( *Vitis vinifera*) Variety Sheegene 102, Australia, PBR No. 2019/025, filed Feb. 20, 2019.
Variety specific information as indicated in transmittal letter of Information Disclosure Statement for U.S. Appl. No. 16/350,751, filed May 8, 2019.

*Primary Examiner* — Annette H Para
(74) *Attorney, Agent, or Firm* — Dentons US LLP

(57) ABSTRACT

'Sheegene 102' is a new grapevine plant with novel characteristics that include medium-large, red seedless grapes that mature in late August to September. The berries produced by 'Sheegene 102' are born on medium-strong woody stems and branches and are well adapted to commercial handling, providing a good fertility.

1 Drawing Sheet

Latin name of the genus and species of the plant claimed: *Vitis vinifera.*

Cultivar denomination: 'Sheegene 102'.

BACKGROUND OF THE INVENTION

The present invention relates to a new distinct variety of grapevine named 'Sheegene 102'. The variety originated from a hybridization performed in Mildura, Victoria, Australia during 2004 between 'Crimson Seedless' (unpatented), as the pollen parent, and 'Red Globe' (unpatented), as the seed parent. The resulting plant was planted in an evaluation block during 2006. The first evaluation of fruit produced by 'Sheegene 102' was performed during 2009. 'Sheegene 102' was first asexually propagated by field grafting dormant hardwood scions to rootstock in 2010 in Irymple, Victoria, Australia. Fruit from the resulting four grafted 'Sheegene 102' vines was first harvested in 2012. All characteristics and distinctions remain true to form and are established and transmitted through succeeding propagations.

SUMMARY OF THE INVENTION

The following are the most outstanding and distinguishing characteristics of 'Sheegene 102'. 'Sheegene 102' produces medium-sized bunches which exhibit a conical shouldered shape and ideal bunch density. The berries produced by 'Sheegene 102' are harvested in late August through September and exhibit an ellipsoidal shape, good size and evenness, and weigh on average 8.5 g/berry. These berries are characterized by their good eating quality, prominent and neutral flavour, and crispy texture.

'Sheegene 102' can be distinguished from its male parent, 'Crimson Seedless', based at least upon vigor, berry size, secondary cluster berry shape, and harvest period. 'Sheegene 102' displays a medium vigor; whereas; 'Crimson Seedless' displays high vigor. The berries produced by 'Sheegene 102' weigh on average 8.5 g/berry; whereas, those produced by 'Crimson Seedless' weigh on average 4 g/berry. Also, the berries within the secondary clusters of 'Sheegene 102' exhibit a more elongated shape than those within the secondary clusters of 'Crimson Seedless'. 'Sheegene 102' is harvested from late August through September, which is earlier than the late September to early November harvest period of 'Crimson Seedless'.

'Sheegene 102' and its female parent, 'Red Globe', both exhibit medium vigor and are harvested mid-season (late August to September). However, 'Sheegene 102' can be distinguished from its female parent, 'Red Globe', based at least upon berry size, shape, seed content, and firmness. The berries produced by 'Sheegene 102' are ovoid, seedless, weigh on average 8.5 g/berry, and are firm and crisp; whereas, those produced by 'Red Globe' are round, contain seeds, weigh on average 10 g/berry, and exhibit medium to low firmness.

BRIEF DESCRIPTION OF THE DRAWING

'Sheegene 102' is illustrated by the accompanying photograph, which shows the form, foliage, and fruit of a 4-year-old vine grown in the field at Murcia, Spain. The colors shown are as true as can be reasonably obtained by conventional photographic procedures.

DETAILED BOTANICAL DESCRIPTION

The following detailed description sets forth the distinctive characteristics of 'Sheegene 102'. The detailed description was obtained between March and November using 4-year-old plants grown in the field at Murcia, Spain. The color references are to the *Munsell Plant Tissue Color Book*, 2012 Edition by Munsell Color.

Classification:
- *Family*.—Vitaceae.
- *Botanical*.—*Vitis vinifera*.
- *Common name*.—Grapevine.
- *Cultivar name*.—'Sheegene 102'.

Plant:
- *Plant habit and growth*.—Semi-erect.
- *Age at maturity*.—4 years old.
- *Size* (*at maturity*).—Height: 225 cm. Width: 300 cm.
- *Vigor*.—Medium.
- *Productivity*.—Very high.
- *Rootstock*.—Name of rootstock: 1103 Paulsen Rootstock. Age of rootstock at time of grafting: one year old.

Trunk:
- *Size*.—Diameter: 9.1 cm.
- *Surface texture*.—Smooth and straight grained with the outer layer easily removed.
- *Bark color*.—Exterior: 10R 6/2. Interior: 2.5YR 5/8.

Canes:
- *Size*.—Diameter: 9 mm. Length: 200 cm.
- *Surface texture*.—Mature cane: smooth. Immature cane: smooth; juvenile shoot is flat and deeply ribbed.
- *Form* (*woody shoot cross section form*).—Circular; pith in center with diaphragm at nodes.
- *Color*.—Mature: 5GY 6/6 at 5 months. Immature: 2.5GY 6/6 at 4 weeks.
- *Internode length* (*upper mature sun cane*).—13.4 cm.

Time of bud burst: March 25.

Tendrils:
- *Form*.—Bifid and trifid.
- *Size*.—Medium/long. Length: 23.1 cm. Diameter: 2.7 mm.
- *Texture and distribution*.—Smooth, curvy at ends; 000000100101111.
- *Color*.—Mature: 2.5GY 7/8 at 4 weeks. Immature: 2.5GY 6/6 at 10 days.
- *Anthocyanin*.—Mature: absent. Immature: present, 10R 6/8.

Growing tips (young shoot):
- *Pubescence*.—Slight to moderate amount.
- *Color*.—2.5GY 8/8.
- *Anthocyanin*.—Present along the edges, 10R 6/8.
- *Shape*.—Wide open.
- *Apex*.—Flat, triangular.

Leaves:
- *Shape*.—Orbicular.
- *Apex*.—Pointed.
- *Base*.—Rounded.
- *Margin*.—Irregular teeth.
- *Length of teeth on margin*.—2-10 mm.
- *Shape of teeth on margin*.—Mostly convex with some straight.
- *Texture* (*mature leaf*).—Upper surface: smooth, flat, slightly bullate along main veins. Lower surface: some cobweb hairs along veins.
- *Size*.—Immature: Length: 5.2 cm at 10 days. Width: 7.0 cm at 10 days. Mature: Length: 13.6 cm at 4 weeks. Width: 18.5 cm at weeks.
- *Color*.—Immature leaf: Upper surface: 5GY 7/8. Lower surface: 5GY 7/8. Mature leaf: Upper surface: 5GY 6/8. Lower surface: 5GY 6/6.
- *Venation*.—Pattern: veins on upper surface are flat; veins on lower surface are raised. Color: Upper surface: 2.5GY 8/8; slight anthocyanin at confluence of veins with petiole, 10R 6/8. Lower surface: 5GY 7/6.
- *Petiolar sinus*.—V-shaped, slight to half open.
- *Petiole*.—Length: 13.3 cm. Diameter: 4 mm. Color: 5GY 6/6; anthocyanin toward base, 5R 5/8.

Floral cluster:
- *General description and location*.—$4^{th}$-$6^{th}$ node; 25% of clusters do not have shoulders.
- *Quantity of inflorescences per cluster*.—150-175.
- *Size*.—Length: 15.8 cm. Width: 7.6 cm (hanging); 13.4 cm (spread).
- *Peduncle*.—Length: 4.8 cm.
- *Inflorescences*.—Hermaphroditic.
- *Stamens*.—Straight, 3.0 mm.
- *Anthers*.—Small, nondescript.
- *Date of bloom*.—Start of bloom, May 5; and 100% bloom, May 12.
- *Pollen amount*.—Moderate.
- *Calyptra*.—5 segments, complete separation.
- *Calyptra color*.—5GY 5/8.

Fruit:
- *Time of year of commercial harvest and shipment*.—Late August.
- *Cluster* (*primary bunches*).—General size: large(863 g). Length (without peduncle): 21 cm. Width: 17.8 cm (hanging), 30.2 cm (spread). Density: medium. Peduncle: Length: 5.4 cm. Diameter: 5.6 mm. Color: 5GY 7/6. Number of berries per cluster: 80-100. Berry: Size: large (8.5 g). Diameter: 20 mm. Length: 29 mm. Shape: ovoid. Uniformity: uniform. Brix content: 17.5° brix. Skin color: 5R 5/10. Pedicel: Length: 8.5 mm. Diameter: 2.3 mm. Color: 5GY 7/6. Strength of attachment to berry: medium.

*Cluster* (*secondary bunches*).—General size: small (61.5 g). Length (without peduncle): 7.4 cm. Width: 7.2 cm (hanging), 10.3 cm (spread). Density: medium. Peduncle. Length: 4.5 cm. Diameter: 2.0 mm. Color: 2.5GY 8/6. Number of berries per cluster: 18. Berry: Size: medium (3.7 g). Diameter: 15.6 mm. Length: 23.9 mm. Shape: elongated ovoid. Uniformity: uniform. Brix content: 18.5° brix. Skin color: 5R 5/10. Pedicel: Length: 6.2 mm. Diameter: 1.8 mm. Color: 2.5GY 8/6. Strength of attachment to berry: medium.

Berry flesh:

*Color*.—2.5GY 8/4.

*Juice color*.—5Y 8/2.

*Juice production*.—Medium, 15% wt/wt.

*Thickness of skin*.—Medium.

*Flavor*.—Neutral.

*Fragrance*.—Neutral.

*Texture*.—Very firm.

*Seeds*.—Rudiments are present (One or two rudiments per berry. Color: 2.5 YR 4/4).

*Use*.—Fresh market.

Disease and insect resistance: The disease and insect resistance of this cultivar is typical of its species.

What is claimed is:

1. A new and *Vitis vinifera* plant named 'Sheegene 102' as shown and described herein.

* * * * *

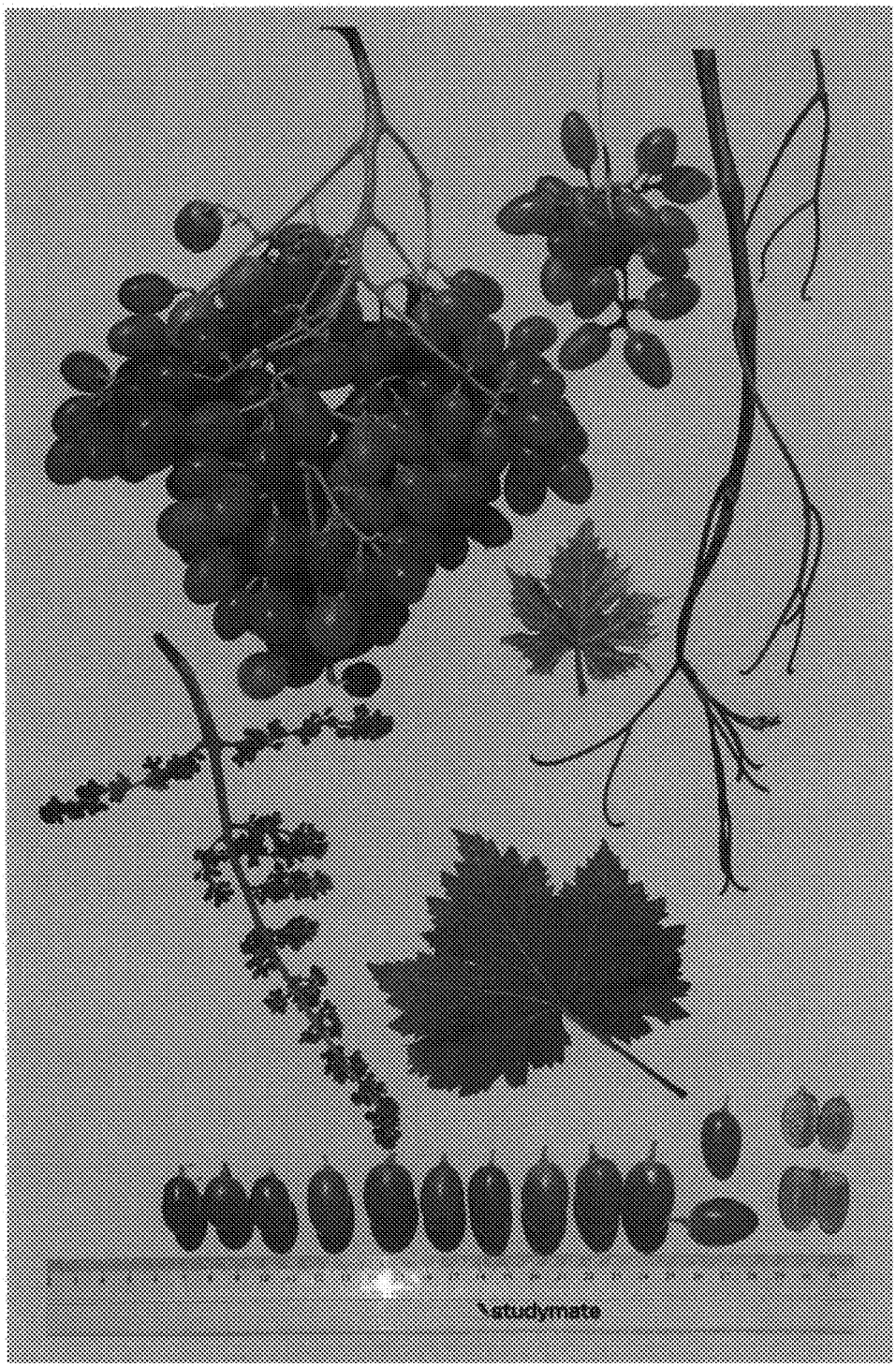
studymate